(12) United States Patent
Muto (10) Patent No.: US 10,524,654 B2
(45) Date of Patent: Jan. 7, 2020

(54) OPHTHALMOLOGIC APPARATUS AND CONTROL METHOD THEREOF, PROCESSING APPARATUS AND PROCESSING METHOD

(71) Applicant: CANON KABUSHIKI KAISHA, Tokyo (JP)

(72) Inventor: Kenji Muto, Fujisawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/667,785

(22) Filed: Mar. 25, 2015

(65) Prior Publication Data
US 2015/0272437 A1     Oct. 1, 2015

(30) Foreign Application Priority Data

Apr. 1, 2014     (JP) ................. 2014-075143

(51) Int. Cl.
| | | |
|---|---|---|
| *A61B 3/12* | (2006.01) | |
| *A61B 3/14* | (2006.01) | |
| *A61B 3/10* | (2006.01) | |

(52) U.S. Cl.
CPC .................................. *A61B 3/102* (2013.01)

(58) Field of Classification Search
CPC .... A61B 3/12; A61B 3/14; A61B 3/10; A61B 3/102
See application file for complete search history.

(56) References Cited

U.S. PATENT DOCUMENTS

| | | | |
|---|---|---|---|
| 2011/0234785 A1* | 9/2011 | Wanda ............... | A61B 3/12 348/78 |
| 2012/0113390 A1* | 5/2012 | Torii ................. | A61B 3/024 351/208 |
| 2012/0320338 A1* | 12/2012 | Hirose ............... | A61B 3/102 351/206 |
| 2013/0002711 A1* | 1/2013 | Sakagawa .......... | A61B 3/0025 345/619 |
| 2013/0039557 A1 | 2/2013 | Wei et al. | |

(Continued)

FOREIGN PATENT DOCUMENTS

| | | |
|---|---|---|
| JP | 2007-252692 A | 10/2007 |
| JP | 2009-089792 A | 4/2009 |

(Continued)

OTHER PUBLICATIONS

Japanese Office Action dated Feb. 15, 2018 and issued in corresponding Japanese Patent Application No. 2014-075143 with English translation.

(Continued)

*Primary Examiner* — William R Alexander
*Assistant Examiner* — Ephrem Z Mebrahtu
(74) *Attorney, Agent, or Firm* — Carter, DeLuca & Farrell LLP (57) ABSTRACT

The present invention provides an ophthalmologic apparatus that includes an acquiring unit that acquires a tomographic image of a fundus of an eye to be inspected, and a display control unit that controls a display unit to display, in a state of corresponding to the acquired image, a comparison area corresponding to another tomographic image to be compared with the acquired tomographic image.

13 Claims, 7 Drawing Sheets

(56) References Cited

U.S. PATENT DOCUMENTS

| | | | | |
|---|---|---|---|---|
| 2014/0204342 A1* | 7/2014 | Higuchi | ................. | A61B 3/102 |
| | | | | 351/208 |
| 2014/0205169 A1* | 7/2014 | Yamakawa | ........... | G06T 7/0012 |
| | | | | 382/131 |
| 2015/0208916 A1* | 7/2015 | Hayashi | ............... | A61B 3/0083 |
| | | | | 351/208 |
| 2016/0302664 A1* | 10/2016 | Yamakawa | .......... | A61B 3/1005 |

FOREIGN PATENT DOCUMENTS

| JP | 2010-142428 A | 7/2010 |
|---|---|---|
| JP | 2010-259629 A | 11/2010 |
| JP | 2011-087672 A | 5/2011 |
| JP | 2011224347 A | 11/2011 |
| JP | 2012-161545 A | 8/2012 |

OTHER PUBLICATIONS

Japanese Office Action dated Aug. 9, 2018 and issued in corresponding Japanese Patent Application No. 2014-075143 with English translation.

\* cited by examiner

OPHTHALMOLOGIC APPARATUS AND CONTROL METHOD THEREOF, PROCESSING APPARATUS AND PROCESSING METHOD

BACKGROUND OF THE INVENTION

Field of the Invention

The present invention relates to an ophthalmologic apparatus exemplified by a fundus examination apparatus used to acquire a tomographic image of the fundus of an eye to be inspected, a control method thereof, a processing apparatus, and a processing method.

Description of the Related Art

In recent years, an apparatus using optical coherence tomography (OCT), which acquires a tomographic image by utilizing the interference of low-coherence light, has been in practical use (hereinafter referred to as the OCT apparatus in some cases). The OCT apparatus allows a tomographic image to be acquired at a resolution of approximately the wavelength of the light incident upon an object to be inspected, thus making it possible to acquire a tomographic image of an object to be inspected with a high resolution. The OCT apparatus is useful especially as an ophthalmologic apparatus for obtaining the tomographic image of the retina positioned on a fundus.

An examiner compares a tomographic image of a subject obtained by the OCT apparatus with a tomographic image of a normative eye or a tomographic image of the same subject acquired in the past thereby to use the result of the comparison as an aid in diagnosis. The comparison is frequently performed on, for example, the thickness of a functional layer (e.g. the thickness of a nerve fiber layer).

Japanese Patent Application Laid-Open No. 2009-89792 describes a technique in which position information for comparing the layer thicknesses of tomographic images is determined, the position information is stored in a normative eye image, a layer thickness corresponding to the position is extracted from an acquired tomographic image, and a difference from the layer thickness of the normative eye is calculated.

SUMMARY OF THE INVENTION

In view of the above, an ophthalmologic apparatus in accordance with the present invention includes: an acquiring unit that acquires a tomographic image of a fundus of an eye to be inspected; and a display control unit that controls a display unit to display, in a state of corresponding to the acquired image, a comparison area corresponding to another tomographic image to be compared with the acquired tomographic image.

Further features of the present invention will become apparent from the following description of exemplary embodiments with reference to the attached drawings.

BRIEF DESCRIPTION OF THE DRAWINGS

FIGS. 2A and 2B illustrate a fundus examination apparatus in the first, a second, and the third embodiments of the present invention, wherein

FIGS. 4A and 4B illustrate examples of macula maps in the first and the third embodiments of the present invention, wherein

DESCRIPTION OF THE EMBODIMENTS

Preferred embodiments of the present invention will now be described in detail in accordance with the accompanying drawings.

To acquire a new tomographic image in order to compare the new tomographic image with the information on a tomographic image that has already been acquired (e.g. a past tomographic image or the two-dimensional map of a normative eye database), it is desirable to acquire the new tomographic image of an area that includes the area of the information on the tomographic image that has already been acquired. For example, to perform comparison according to a macula map, it is desirable to acquire a new tomographic image of an area that includes an area of a macula map corresponding to a tomographic image that has already been acquired (e.g. a macula map of the normative eye database).

However, in acquiring a new tomographic image, a conventional apparatus is not devised to acquire the new tomographic image in an area that includes information on the tomographic image that has already been acquired and does not suggest the need therefore. Especially, the area of a tomographic image is recently expanding, so that the need for devising efforts is increasing.

One object of the present embodiment is to provide display that aids a user by enabling the user to acquire a new tomographic image of an area that includes information on a tomographic image that has already been acquired (e.g. a past tomographic image or the two-dimensional map of a normative eye database). The embodiments are capable of providing display that aids a user by enabling the user to acquire a new tomographic image of an area that includes information on a tomographic image that has already been acquired (e.g. a past tomographic image or the two-dimensional map of a normative eye database). The information on a tomographic image that has already been acquired may be any other tomographic image to be compared with a tomographic image to be newly acquired. The following will describe in detail the embodiments with reference to the accompanying drawings.

[First Embodiment]

A first embodiment of the present invention will be described below with reference to the accompanying drawings. In the present embodiment, a fundus examination apparatus, which is an embodiment of an ophthalmologic apparatus, will be described. In performing comparison using a macula map, the fundus examination apparatus according to the present embodiment is capable of imaging an area that is certain to include the area of the map.

(Schematic Configuration of the Apparatus)

Figure 2A:
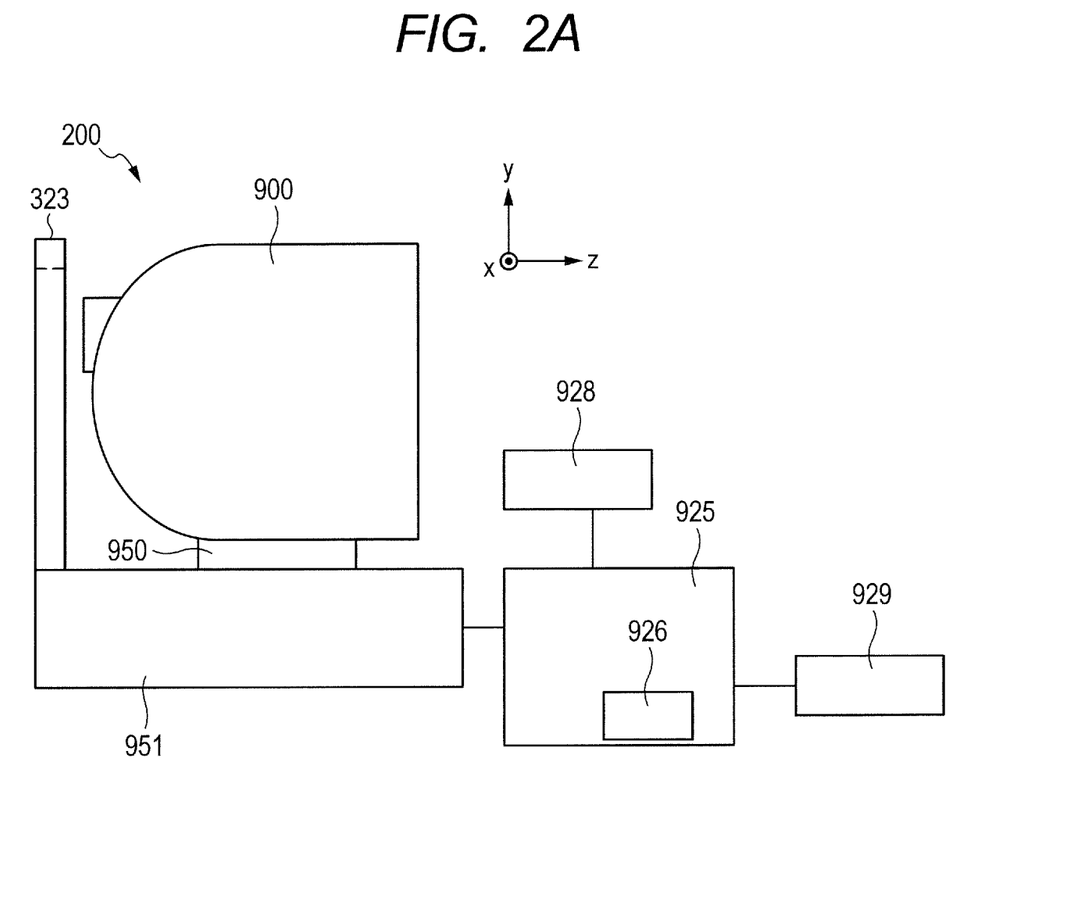
FIG. 2A is a schematic side view of the fundus examination apparatus and FIG. 2B schematically illustrates an optical system incorporated in an optical head in the fundus examination apparatus.

The schematic configuration of the fundus examination apparatus according to the present embodiment will be described with reference to FIG. 2A and FIG. 2B. FIG. 2A is a side view of an ophthalmologic apparatus. A fundus examination apparatus 200 includes an optical head 900, a stage 950, a base 951, and a control part 925. The optical head 900 is a measurement optical system for acquiring an anterior ocular image and the two-dimensional image and the tomographic image of a fundus. The stage 950 is a moving part adapted to make the optical head 900 movable in directions x, y and z in the drawing by using a motor (not illustrated). The base 951 incorporates a spectroscope, which will be discussed later.

The control part 925 is a personal computer that serves also as a control part of the stage, and mainly controls the stage and constructs tomographic images. A hard disk 926 stores the information on subjects and also stores a program for acquiring tomographic images, and is included in the control part 925. The hard disk 926 stores a plurality of normative eye tomographic images in addition to the information on subjects, and also stores the statistical data, such as the average values and distributions of the thicknesses of retinal layers, obtained from the groups of the tomographic images. The tomographic images of the normative eyes and the statistical data will be generically referred to as the normative eye database. An object to be compared in the present embodiment refers to the normative eye database. The fundus examination apparatus compares a tomographic image of a subject obtained by an examination and a value of interest with the normative eye database, thereby providing an aid in diagnosis.

A display 928 is a monitor of the personal computer. Instructions are input to the personal computer through an input part 929. The input part 929 is constituted of, specifically, a keyboard and a mouse. A chin rest 323 is adapted to secure chin and the forehead of a subject thereby to facilitate the fixation of an eye (an eye to be inspected) of a subject.

(Configurations of the Measurement Optical System and the Spectroscope)

Figure 2B:
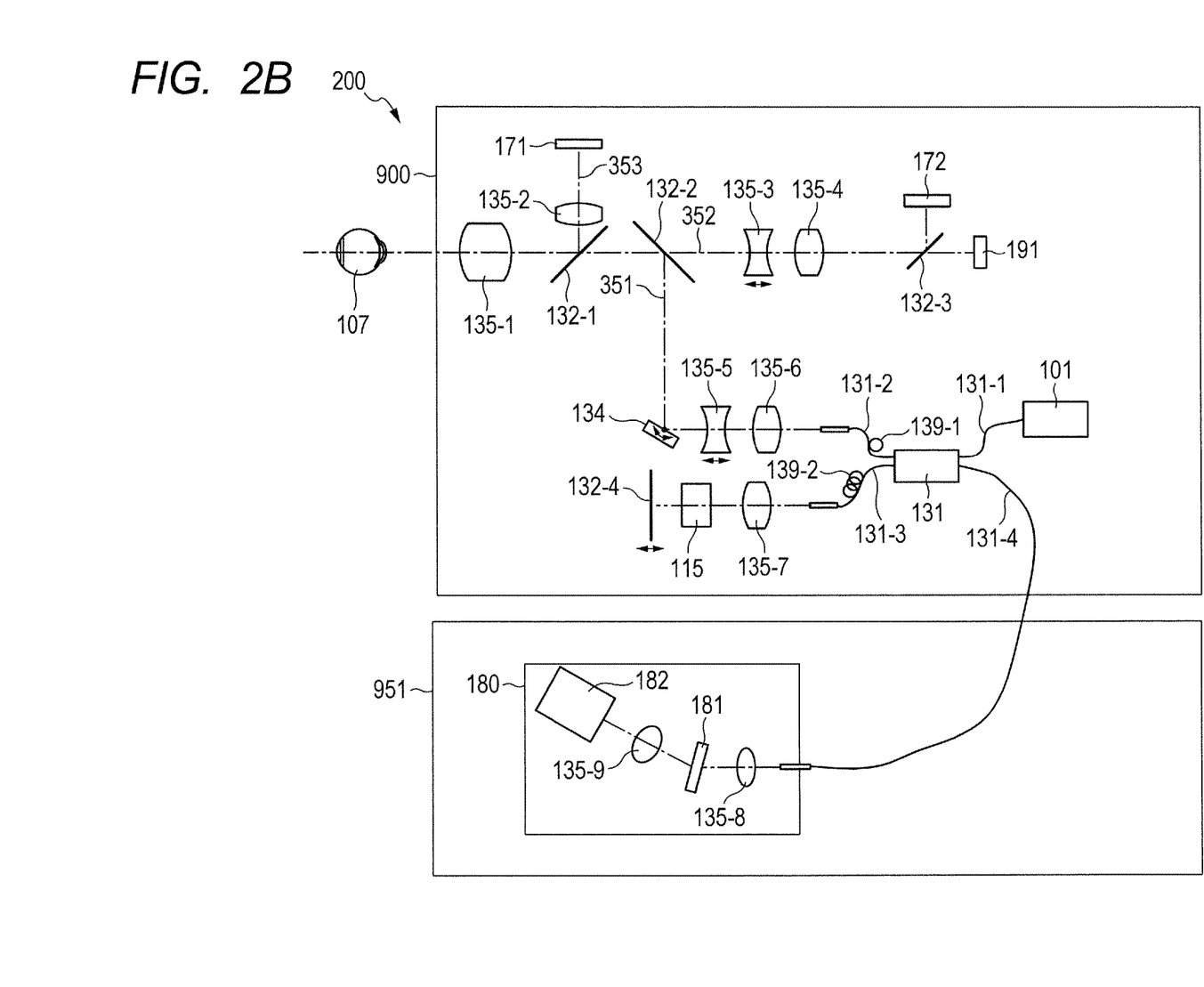

Referring to FIG. 2B, the configurations of the measurement optical system and the spectroscope of the present embodiment will be described.

First, the interior of the optical head 900 will be described. An objective lens 135-1 is installed, opposing an eye 107 to be inspected, and a first dichroic mirror 132-1 and a second dichroic mirror 132-2 are disposed on the optical axis of the objective lens 135-1. The optical path from the eye to be inspected is branched according to wavelength band into an optical path 353 for anterior ocular observation by the second dichroic mirror. Thereafter, the optical path is further branched by the first dichroic mirror into an optical path 351 of an OCT optical system and an optical path 352 for fundus observation and a fixation lamp by each wavelength band, The optical path 352 is further branched by a third dichroic mirror 132-3 into a optical path leading to a CCD 172 for fundus observation and a optical path leading to a fixation lamp 191 also by each wavelength band. Here, a lens 135-3 and a lens 135-4 are disposed on the optical path 352, and the lens 135-3 is driven by a motor (not illustrated) for focusing for the fixation lamp and fundus observation. The CCD 172 has sensitivity to a wavelength of illuminating light for the fundus observation (not illustrated), specifically, the vicinity of 780 nm. Meanwhile, the fixation lamp 191 emit visible light, facilitating visual fixation of a subject.

A lens 135-2 and an infrared CCD 171 for anterior ocular observation are disposed on an optical path 353. The CCD 171 has sensitivity to a wavelength of illuminating light for the anterior ocular observation (not illustrated), specifically, the vicinity of 970 nm.

As described above, the optical path 351 constituting the OCT optical system is adapted to acquire a tomographic image of the fundus of the eye 107 to be inspected, and constitutes a fundus image acquiring part that acquires a tomographic image of the fundus of the eye to be inspected. More specifically, the optical path 351 is adapted to obtain an interference signal for forming a tomographic image. An XY scanner 134 disposed on the optical path 351 scans light on a fundus. The XY scanner 134 illustrated as a single mirror is adapted to perform scanning in the directions of two axes, X and Y. From the end of the eye 107 to be inspected, the XY scanner 134 is disposed and a lens 135-5 and a lens 135-6 follow. The lens 135-5 is driven by a motor (not illustrated) to focus the light from a light source 101, which exits from a fiber 131-2 connected to an optical coupler 131, onto the eye 107 to be inspected. The focusing causes the light from the eye 107 to be inspected to be formed into a spot image and enter the distal end of the fiber 131-2.

The description will now be given of the optical path from the light source 101 and the configurations of a reference optical system and the spectroscope.

The reference optical system has an optical fiber 131-1, an optical coupler 131, an optical fiber 131-3, a lens 135-7, a dispersion compensation glass 115, and a mirror 132-4, which are disposed in order from the light source 101. The foregoing optical coupler 131 has single-mode optical fibers 131-1 to 131-4, which are connected thereto into one unit. Further, the optical fiber 131-4 is connected to a spectroscope 180.

Thus, the Michelson interferometer is constructed. The light emitted from the light source 101 passes through the optical fiber 131-1 to be divided through the optical coupler 131 into measurement light on the optical fiber 131-2 side and reference light on the optical fiber 131-3 side. The measurement light is irradiated to the fundus of the eye 107 to be inspected, which is the object to be observed, through the optical path 351 of the foregoing OCT optical system and reaches the optical coupler 131 through the same optical path as return light by being reflected or diffused by a retina.

Meanwhile, the reference light passes through the optical fiber 131-3, the lens 135-7, and the dispersion compensation glass 115 inserted to adjust the dispersion of the measurement light and the reference light and reaches the mirror 132-4 to be reflected. Then, the reflected reference light traces the same optical path back to the optical coupler 131.

The optical coupler 131 combines the measurement light and the reference light into interference light. When the optical path length of the measurement light and the optical path length of the reference light become substantially the same, the interference takes place. The mirror 132-4 is adjustably held in an optical axis direction by a motor and a driving mechanism (not illustrated), making it possible to adjust the optical path length of the reference light to the optical path length of the measurement light that changes according to the eye 107 to he inspected. The interference light is led to the spectroscope 180 through the optical fiber 131-4.

Further, a polarization adjusting part 139-1 on the measurement light side is provided in the optical fiber 131-2. Similarly, a polarization adjusting part 139-2 on the reference light side is provided in the optical fiber 131-3. These polarization adjusting parts have some portions in which the optical fibers are looped, the looped portions being turned about the longitudinal direction of the optical fibers. Adding the twist to the optical fibers makes it possible to adjust and match the polarizations of the measurement light and the reference light. In the present apparatus, the polarizations of the measurement light and the reference light are adjusted and fixed in advance.

The spectroscope 180 is constituted of lenses 135-8 and 135-9, a diffraction grating 181, and a line sensor 182.

The interference light emitted from the optical fiber 131-4 is turned into parallel light through the lens 135-8, dispersed by the diffraction grating 181, and formed into an image on the line sensor 182 through the lens 135-9.

The periphery of the light source 101 will now be described. The light source 101 uses a super luminescent diode (SLD), which is a typical low-coherent light source. The central wavelength is 855 nm, and the wavelength band width is approximately 100 nm. The band width is an important parameter, because the band width influences the resolution in the optical axis direction of a tomographic image to be obtained. As the type of the light source, the SLD has been selected in this case; however, other type, such as an amplified spontaneous emission (ASE), may be used insofar as low-coherent light can be emitted. For the measurement of an eye, near infrared light is suited for the central wavelength. Further, the central wavelength influences the resolution in the lateral direction of a tomographic image to be obtained, so that the central wavelength is preferably a short wavelength as much as possible. For the two reasons described above, the central wavelength of the measurement light in the present embodiment has been set to 855 nm.

The Michelson interferometer has been used as the interferometer in the present embodiment; instead, however, the Mach-Zehnder interferometer may be used. Preferably, according to the difference in the amount of light between the measurement light and the reference light, the Mach-Zehnder is used when the difference in the amount of light is large, and the Michelson interferometer is used when the difference in the amount of light is relatively small.

(Method of Acquiring a Tomographic Image)

The description will be given of a method of acquiring a tomographic image by using the fundus examination apparatus 200. The fundus examination apparatus 200 is capable of acquiring a tomographic image of a desired portion of a fundus of the eye 107 to be inspected by controlling the XY scanner 134.

First, measurement light scan in the direction x in FIG. 2A is carried out to acquire, by the line sensor 182, the information equivalent to a predetermined number of imaging lines from an image acquisition area in the direction x in a fundus. The luminance distribution on the line sensor 182 obtained at a certain position in the direction x is subjected to the fast Fourier transform (FFT), and the linear luminance distribution obtained by the FFT is transformed into density or color information to be displayed on the display 928. The obtained result is referred to as the A scan image. A two-dimensional image formed of a plurality of the A scan images arranged is referred to as the B scan image. After acquiring a plurality of the A scan images to constitute a single B scan image, the scan position in the direction y is changed, and the scan in the direction x is carried out again, thereby acquiring a plurality of the B scan images. The plurality of the B scan images or a three-dimensional tomographic image created from the plurality of the B scan images is displayed on the display 928, thus enabling an examiner to use the obtained images or image to diagnose the eye to be inspected.

(Flow of Acquiring a Tomographic Image)

The flowchart of the image acquiring process illustrated in FIG. 3 will be described in the order of the steps.

The image acquiring is started in step 1001. An image acquiring program is executed by the control part 925, starting up an image acquiring screen on the display 928. At the same time, the XY scanner 134 is actuated. Thereafter, the flow automatically proceeds to step 1002.

In step 1002, the display 928 shows a patient information input screen. The examiner selects a patient, or enters the information on a patient in the case of a first visit. An operation by the examiner (e.g. clicking with a mouse an OK button displayed on the patient information input screen) causes the flow to proceed to step 1003.

Figure 1:
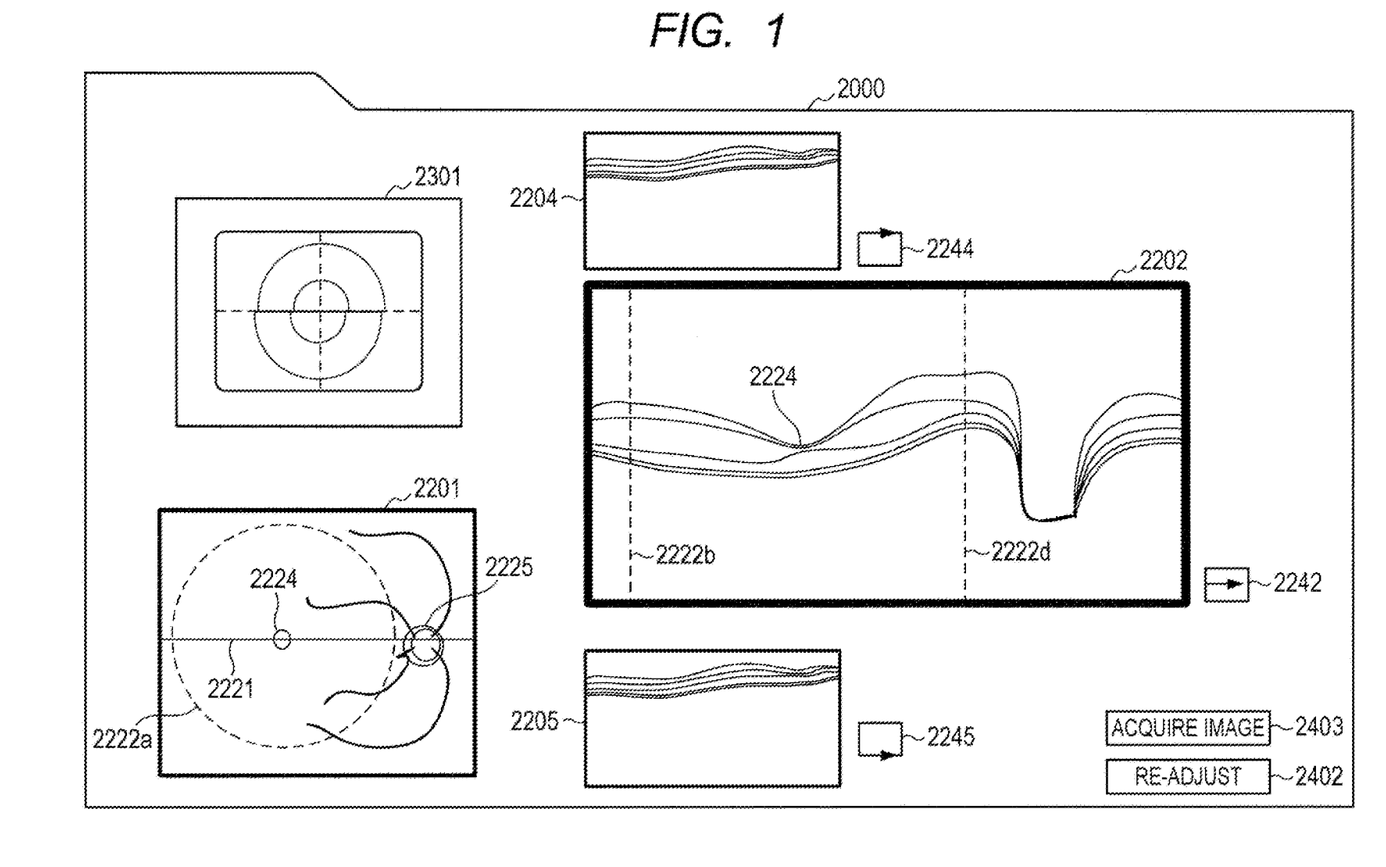
FIG. 1 is a diagram illustrating an image acquiring adjustment screen in a first and a third embodiments of the present invention.

In step 1003, the display 928 shows an examination parameter selection screen, on which the examiner sets examination parameters, such as which of the right and the left eye is to be examined, the area of a tomographic image, the number of times the tomographic images is to be acquired, and the number of the A scan images to be included in the B scan image. Further, it is also selected at this time whether to carry an examination that involves comparison with the normative eye database. Then, an operation by the examiner (e.g. clicking with the mouse the OK button displayed on the examination parameter selection screen) causes the flow to proceed to step 1004.

in step 1004, the optical head 900 is moved to an initial alignment position. At the same time, an image acquiring adjustment screen, i.e. an adjustment screen in the present embodiment, is shown on the display 928. FIG. 1 illustrates an example of an image acquiring adjustment screen 2000. More specifically, in this step, the optical head 900 is moved to a measurement start position according to whether the right or the left eve is to he examined, and an image of the anterior ocular part of the eye 107 to be inspected is acquired by the CCD 171 for anterior ocular observation. An anterior ocular part image 2301 is displayed on the image acquiring adjustment screen 2000 in FIG. 1. The image acquiring adjustment screen 2000 may alternatively be designed to display at least one of a fundus image and a tomographic image for adjustment. In this case, the display control unit, which will be discussed later, shows on the display 928 a comparison area to be compared with at least one of the fundus image and the tomographic image for adjustment after a tomographic image is acquired. The display 928 functions as a display part capable of displaying a tomographic image and a fundus image of an eye to be inspected. Alternatively, however, the display 928 may be configured to be a separate unit that displays, for example, a signal obtained wirelessly or the like. Further, as a display mode, a comparison area may be displayed by being superimposed, and other display mode, such as arrows shown outside an image, may be used insofar as individual positional relationships can be associated and displayed.

Next, the optical head 900 is moved by the above-described control part in the directions x and y such that the center of a pupil, which provides an initial adjustment target position, agrees with an image center position in the anterior ocular part image 2301. The position of the optical head 900 in the direction z is adjusted such that pupil images vertically divided are laterally aligned.

Thereafter, the flow automatically proceeds to step 1005.

In step 1005, the previews of a fundus image and a tomographic image are displayed on the display 928. The image acquiring adjustment screen 2000 in FIG. 1 illustrates a preview 2201 of the fundus image and the previews 2202, 2204 and 2205 of the tomographic images. Each of the previews is an animated image, and the image is updated moment to moment. The tomographic image preview 2202 is a tomographic image preview at a line 2221 at the center in the horizontal direction of the fundus image preview 2201. Further, the tomographic image preview 2204 is a tomographic image preview at the upper edge of the fundus image preview 2201, and the tomographic image preview 2205 is a tomographic image preview at the lower edge of the fundus image preview 2201.

Indicators 2242, 2244, and 2245 schematically indicate the positions of the tomographic image previews 2202, 2204, and 2205 on the fundus image preview 2201.

A description will now be given of a case were an examination that involves the comparison with the normative eye database has been selected in step 1003. The selection indicates an acquiring condition for acquiring or when having acquired a tomographic image input by the examiner, and whether a comparison area is to be displayed or not, to be determined according to the condition. In this case, the fundus image preview 2201 shows a comparison area 2222*a* based on the size of a macula map in the normative eye database. The map has a circular outer periphery and has a macula at the center thereof. The macular map in the normative eye database will be described in detail later. Hence, the comparison area 2222*a* is also circular, having the same diameter, and displayed so as to be positioned with a macula 2224 at the center thereof.

The image acquiring program includes a macula position detecting means as a characteristic spot detecting means or a characteristic area detecting means to detect the position of the macula. The macula position detecting means recognizes an image from a tomographic image preview and detects the position of the center of a recession of the macula 2224 as the characteristic area in the tomographic image. In the present embodiment, the center of the comparison area 2222*a* is assumed to be located at the same position as the detected coordinate position of the macula on the tomographic image preview 2202, and the comparison area 2222*a* is displayed, being superimposed.

Further, comparison area boundaries 2222*b* and 2222*d* are displayed on the tomographic image preview 2202, also being superimposed at the positions corresponding to the boundaries of the comparison area 2222*a* displayed on the fundus image preview 2201. The comparison area or the comparison area boundaries on the preview may be displayed on all previews or on any one preview in particular, the inclusion or exclusion of which must be determined.

As described above, a comparison area based on another tomographic image, which is to be compared with an acquired tomographic image, is superimposed on at least one of the acquired tomographic image and fundus image, and displayed on the display 928. The operation is performed by a module area that functions as a display control unit in the control part 925. Further, as described above, the display control unit also performs an operation for displaying the image acquiring adjustment screen 2000 on the display 928 when acquiring a plurality of tomographic images of a scan area on a fundus predetermined by the fundus tomographic image acquiring part, i.e. the acquiring unit. Further, the display control unit determines the position of the superimposition of a comparison area in a tomographic image and a fundus image according to a characteristic area detected the foregoing characteristic area detecting means.

If the coordinates of a comparison area deviate from the coordinates of a tomographic image area, then the determining means, which is provided in the image acquiring program and which determines the position of the comparison area, determines that the comparison area 2222*a* will be out of the tomographic image area to be acquired. In other words, the determining means determines whether or not the comparison area will be included in the acquisition area of an acquired tomographic image. Further, based on the determination result, an alarm is issued on the adjustment screen to notify the examiner of the error. This is accomplished by, for example, displaying the comparison area 2222*a* and the comparison area boundaries 2222*b* and 2222*d* in red or displaying a message. If such an alarm is issued, the examiner changes the position of an internal fixation lamp by an internal fixation lamp position specifying means (not illustrated) on the adjustment screen 2000 thereby to change the line of sight of the subject. The line of sight of the subject is changed to change the position of the tomographic image acquisition area so as to make an adjustment such that the comparison area 2222*a* falls within the tomographic image area. The internal fixation lamp position specifying means corresponds to the changing means for changing she position of the tomographic image acquisition area in the present embodiment.

At the same time, in the step 1005, the adjustment of the optical path length of the reference optical path by moving the mirror 132-4, focusing on a fundus image through the lens 135-3, and focusing on a tomographic image through the lens 135-5 are automatically carried out.

In step 1006, it is determined whether or not an input is received from the examiner to start the acquisition of a tomographic image. If the input is received from the examiner, who clicks with a mouse an image acquisition button 2403 on the adjustment screen 2000, then the flow proceeds to step 1007. If the examiner performs an input operation by clicking with the mouse a readjustment button 2402 to readjust the automatic adjustments so as to improve a tomographic image, rather than performing the input operation for starting the acquisition, then the flow proceeds to step 1012. In this step 1012, instructed movements are carried out at specified adjustment locations. After the adjustments are performed, the flow proceeds to step 1006 to stand by again for the input for starting the acquisition.

In step 1007, a tomographic image is acquired under an acquiring condition set in step 1003. At the same time, the tomographic image is stored together with a fundus image, which is acquired by the CCD for fundus observation, in the memory of the control part 925. The storing operation may be accomplished automatically or by clicking with the mouse an image acquisition button displayed on the screen. Thereafter, the flow automatically proceeds to step 1008.

In step 1008, the acquired tomographic image is displayed. This display screen is an acquired image checking screen that enables the examiner to determine whether or not the acquired image is an error. This screen will be discussed in detail later.

In step 1009, the flow stands by for an input from the examiner indicating whether or not the acquired tomographic image is an error. If the acquired tomographic image is not an error, then the OK button on the screen is clicked with the mouse, and the flow proceeds to step 1010 in response to the input. If the acquired tomographic image is an error, then an NG button on the screen is clicked with the mouse, and the flow proceeds to step 1013 in response to the input.

In step 1013, an error flag is added to the stored tomographic images data. This is to notify the examiner of the error by displaying that the tomographic image is an error when the tomographic image is read out in the future. Then, the flow automatically proceeds to step 1010.

In step 1010, a screen for selecting whether to continue or end the image acquisition is displayed for the examiner to select therebetween. If continuing the image acquisition is selected, then the flow proceeds to step 1003, or if ending the image acquisition is selected, then the flow proceeds to step 1011 to terminate the examination. The above has described the flow of acquiring images in the fundus examination apparatus according to the present embodiment.

(Comparison with the Macula Map)

Figure 4A:
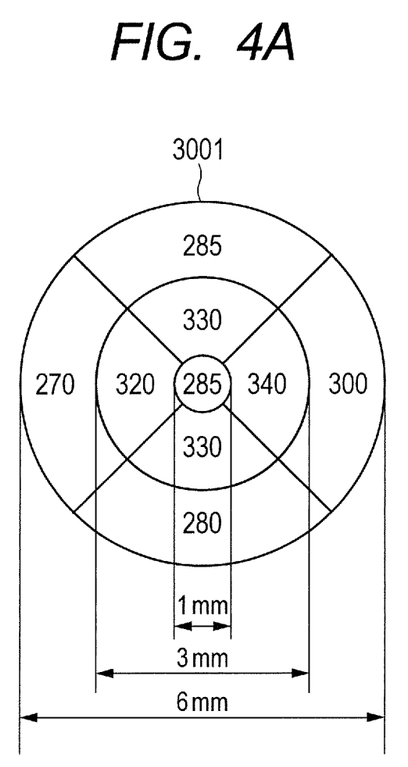
FIG. 4A illustrates an example of a map used for a macular disease.
Figure 4B:
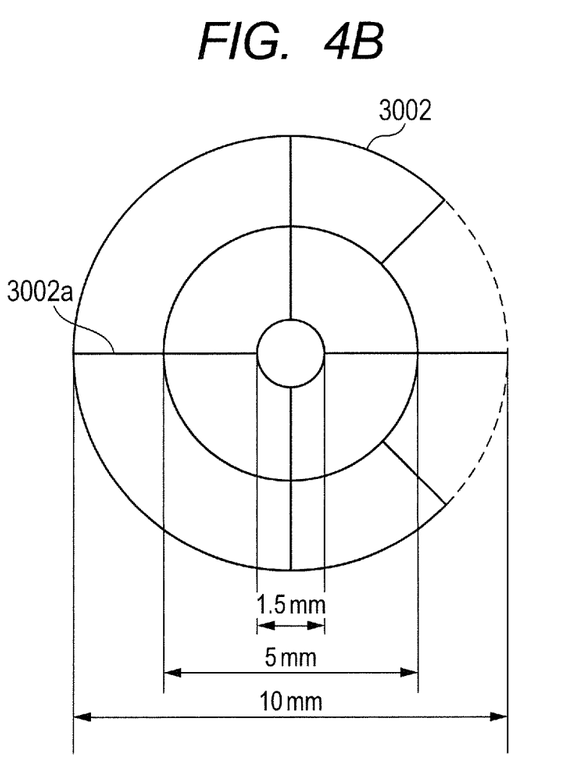
FIG. 4B illustrates an example of a map used for a glaucoma disease.

Referring to FIG. 4A and FIG. 4B, the comparison with the macula map in the present embodiment will be described. FIG. 4A illustrates an example of a map area for diagnosing the macula disease, and FIG. 4B illustrates an example of a map area for diagnosing the glaucoma disease.

A macula disease diagnosis map 3001 is formed of nine sectors defined by three circles, which are concentric about the macula and which have diameters of 1 mm, 3 mm and 6 mm, respectively, and straight lines in the directions of ±45 degrees. In FIG. 4A, the mean value in each sector of a retinal layer thickness of examination data is indicated in units of μm.

The comparison with the retinal layer thickness statistic data of a normative eye on the normative eye database is carried out and the result is displayed by a color in each sector. For example, the sectors of data in the distribution of 5% to 95% relative to the retinal layer thickness of a normative eye are indicated by green, the sectors of data in the distribution of 1% to 5% and 95% to 99% are indicated by yellow, the sectors of data in the distribution of 99% to 100% are indicated by pink, and the sectors of data in the distribution of 0% to 1% are indicated by red. This enables the examiner to visually recognize the numerical values of the examination data relative to the data distribution of the normative eye, thus aiding the diagnosis.

More directly, the deviation from the mean value of the normative eye can be displayed in each sector. Further, in addition to the retinal layer thickness, the thickness of each recognizable layer or the total of the thicknesses of some layers can also be displayed and compared. For example, the total value of the thickness of a nerve fiber layer, the thickness of a ganglion cell layer, and the thickness of an inner plexiform layer (three layers of the retina inner layer) is frequently used in recent years.

A glaucoma disease diagnosis map 3002 is formed of nine sectors defined by three circles, which are concentric about a macula and which have diameters of 1 mm, 5 mm and 10 mm, respectively, and straight lines in the directions of ±90 degrees and straight lines in the directions of ±45 degrees, as illustrated. The missing portion of the sector defined by the circles having the diameters 5 mm and 10 mm indicates the vicinity of optic papilla. As with the macula disease diagnosis map, each sector shows a value, which is omitted in the drawing. Further, an axis 3002a is disposed, coinciding with a line that connects the center of the macula and the center of the papilla. As with the macula disease diagnosis map, the layer thicknesses or the differences in layer thickness from the normative eye database are indicated by the colors in the sectors based on the comparison with the normative eye database. The center of the macula is detected as described above. The image acquiring program further includes a papilla center position detecting means as another characteristic area detecting means. The papilla center position detecting means extracts the shape of the optic papilla from the layer information of a tomographic image, determines the position of the center of gravity thereof as the center of the papilla, and stores the position on the image as the center of the papilla.

The comparison area 2222a shown in the fundus image preview 2201 and the comparison area boundaries 2222b and 2222d shown in the tomographic image preview 2202 in FIG. 1 are displayed such that the outer boundaries of the foregoing map are indicated, centering around the macula. Although FIG. 1 illustrates only the outer boundaries, the nine sectors themselves may alternatively be illustrated. Further alternatively, the layer thicknesses or the values from the comparison with the normative eye database, and the sectors colored on the basis of the comparison results may be shown in the previews.

Further, as described above, the center of the macula and the center of the papilla have been detected, so that the distance between the center of the macula and the center of the papilla can be calculated. Hence, when displaying, for example, the comparison areas relative to the glaucoma disease diagnosis map in the preview, the map can be changed according to a distance $L_{m-d}$ between the center of the macula and the center of the papilla. In this case, a diameter $2.5 \times L_{m-d}$, which is determined by the distance ratio between the center of the macula and the center of the papilla $L_{m-d}$, is displayed rather than the diameter of 10 mm illustrated in FIG. 4B.

(Alarm Upon Replication in Tomographic Image)

It has been described above that an alarm is issued if the comparison area 2222a extends beyond the tomographic image area to be acquired. In the present embodiment, an alarm can also be displayed if a replication of a tomographic image occurs in a comparison area.

Figure 7:
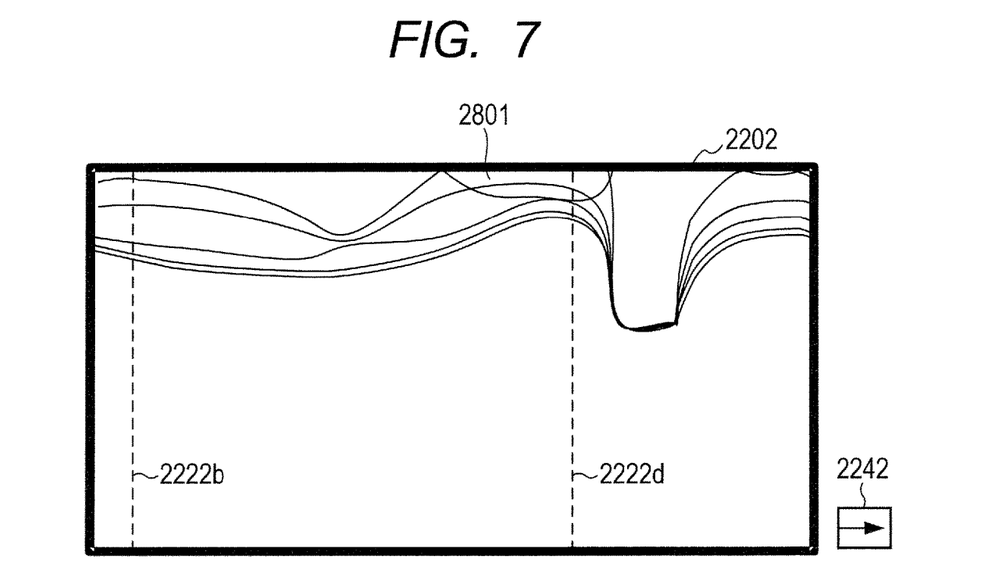
FIG. 7 illustrates a case where a replication image appears in a comparison area.

This will be described with reference to FIG. 7. FIG. 7 illustrates an example in which replication of a tomographic image has appeared in a comparison area. The term "replication" refers to a phenomenon that takes place when a reference mirror reaches a position that is optically equivalent to the inside of the retinal layer. FIG. 7 illustrates the case where a mirror image 2801 of the tomographic image that is symmetrical with respect to the upper side of the tomographic image preview 2202 has appeared in the tomographic image preview.

Using such a tomographic image tends to lead to a failure in recognizing a retinal layer, typically resulting in a calculated layer thickness that is different from an actual layer thickness. For this reason, the use of such a tomographic image should be avoided especially when the obtained result is to be compared with the normative eye database.

To avoid such a problem, the image acquiring program is desirably provided with a replication determination means. The replication determination means calculates, for each A scan image, a value by adding the luminance value of the tomographic image in the direction of the retinal thickness. If the replication determination means detects that discontinuity has occurred in the horizontal direction (the direction of the B scan) of a tomographic image, then the replication determination means determines that there is a replication in the tomographic image and displays an alarm. The alarm display prompts the examiner to readjust the position of the reference mirror.

The readjustment may be performed by the examiner, or the reference mirror may be minutely moved in both directions. Alternatively, the foregoing determination may be repeated and the reference mirror position may be automatically adjusted so as to avoid the replication.

(Automatically Adjusting the Tomographic Image Scan Position)

It has been described above that the position of the internal fixation lamp is changed by an operation performed by the examiner in the case where the comparison area 2222a extends beyond a tomographic image area to be acquired. Alternatively, however, the operation may be automatically Performed. In this case, for example, the position of the internal fixation lamp may be automatically adjusted by minutely changing the position of the internal fixation lamp and the foregoing determination of the position of the comparison area each time the position thereof is changed so as to prevent the comparison area from extending beyond the tomographic image area to be acquired. Alternatively, the position of the scanning center of the XY scanner 134 rather than the position of the internal fixation lamp may be changed to avoid the problem. This may be operated by the examiner or may be automatically adjusted, as with the readjustment of the position of the internal fixation lamp.

[Second Embodiment]

The fundus examination apparatus according to the present embodiment differs from the first embodiment only in the aspect in which the layer thickness at the position on a circle at the center of the papilla is compared rather than using the macula center map. The schematic configuration of the apparatus, the configurations of the measurement optical system and the spectroscope, and the method for acquiring tomographic images are the same as those in the first embodiment, so that the descriptions thereof will be omitted.

(Flow of Acquiring a Tomographic Image)

Figure 3:
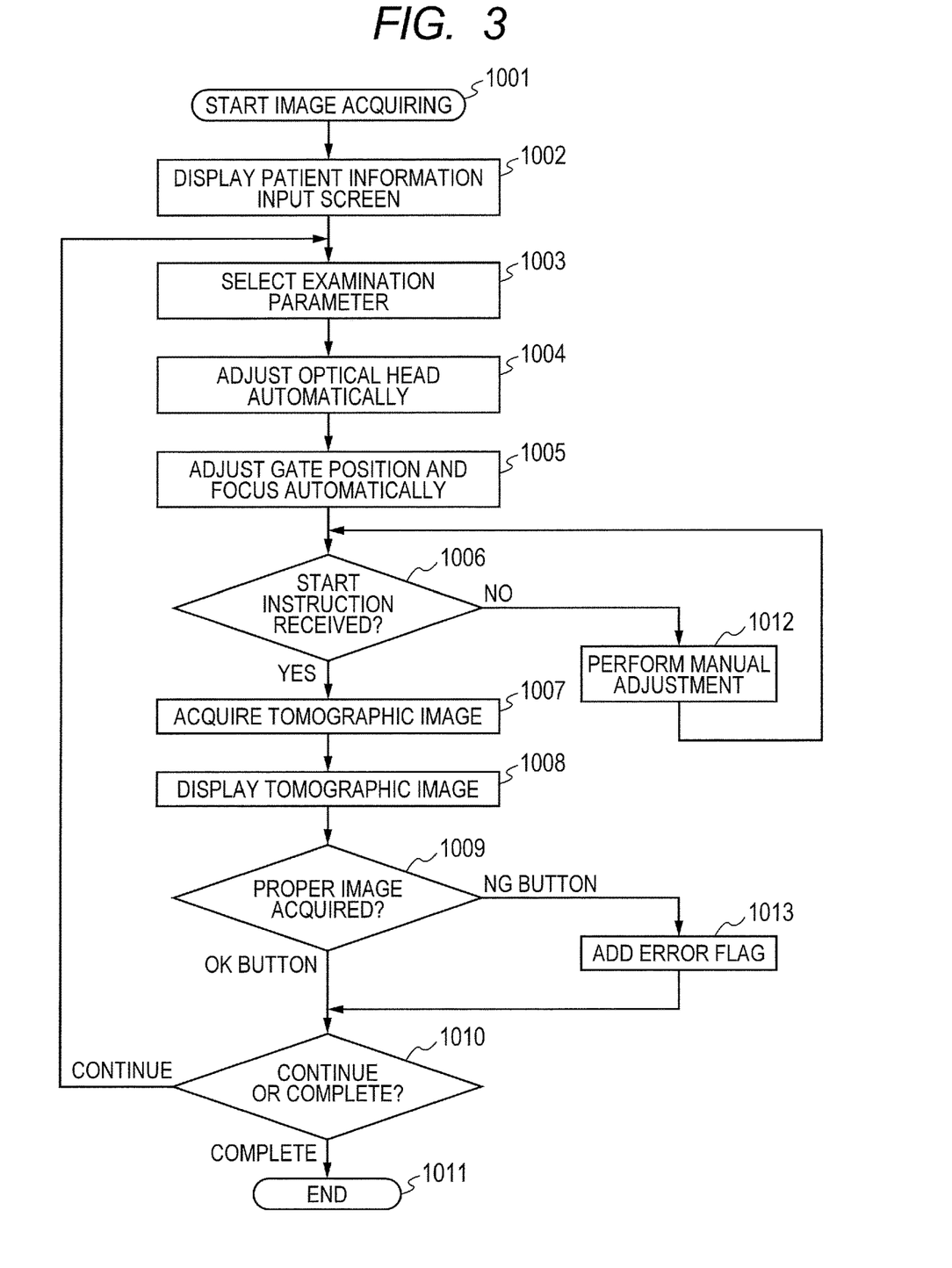
FIG. 3 is a flowchart illustrating an image acquisition flow in the first, the second and the third embodiments of the present invention.

The schematic image acquisition flow of the second embodiment is substantially the same as the image acquisition flow of the first embodiment illustrated in FIG. 3 except for step 1005. Hence, the description will be given of step 1005 below.

According to the present embodiment, the previews of a fundus image and a tomographic image are displayed on a display 928 in step 1005. A fundus image preview 2201 and tomographic image previews 2202, 2204 and 2205 are displayed on an image acquiring adjustment screen 2000 illustrated in FIG. 5. Each of the previews is an animated image, and the image is updated every moment. The tomographic image preview 2202 is a tomographic image preview at a line 2221 at the center in the horizontal direction of the fundus image preview 2201. Further, the tomographic image preview 2204 is tomographic image preview at the upper edge of the fundus image preview 2201, and the tomographic image preview 2205 is a tomographic image preview at the lower edge of the fundus image preview 2201.

Figure 5:
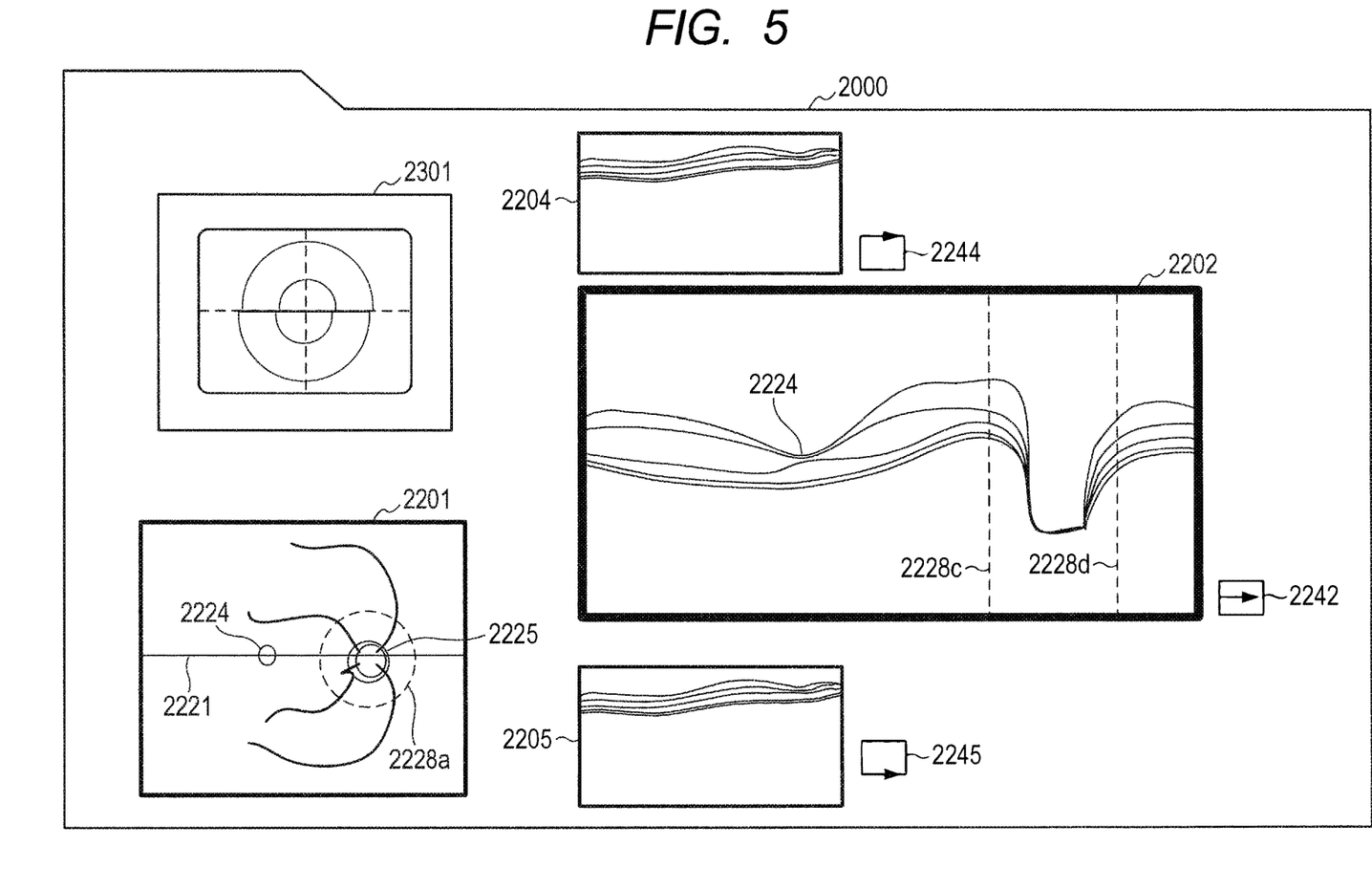
FIG. 5 illustrates an image acquiring adjustment screen in the second and the third embodiments of the present invention.

Indicators 2242, 2244 and 2245 schematically indicate the positions of the tomographic image previews 2202, 2204, and 2205 on the fundus image preview 2201.

The following will describe case where an examination that involves the comparison with a normative eye database has been selected in step 1003. In this case, a comparison area 2228a based on the profile area circle of a papilla neural fiber layer in a normative eye database is displayed on the fundus image preview 2201. The profile area is formed of a circle having a diameter of 3.45 mm, the center thereof being the center of the papilla. The details of the profile of the papilla neural fiber layer in the normative eye database will be described later. Hence, the comparison area 2228a is formed of a circle having the same diameter, and displayed such that the comparison area 2228a is positioned, centering about the papilla 2225. An image acquiring program is provided with a papilla center Position determining means as a characteristic area detecting means to detect the position of the center of the papilla. The papilla center position determining means determines the center of the papilla from a tomographic image preview and determines the coordinate of the center of the papilla.

According to the present embodiment, the center of the comparison area 2228a is assumed to be located at the same position as the coordinate of the position of the center of the papilla on the fundus image preview 2201, which has been detected, and the comparison area 2228a is superimposed thereon and displayed.

Further, comparison area boundaries 2228c and 2228d are displayed on the tomographic image preview 2202, also being superimposed at the positions corresponding to the boundaries of the comparison area 2228a displayed on the fundus image preview 2201.

The alarm issued if the comparison area 2228a extends beyond a tomographic image acquisition area, the correction thereof or adjustments are the same as those of the first embodiment, so that the descriptions thereof will be omitted.

(Comparison of the Papilla Neural Fiber Layer Profile)

Figure 6:
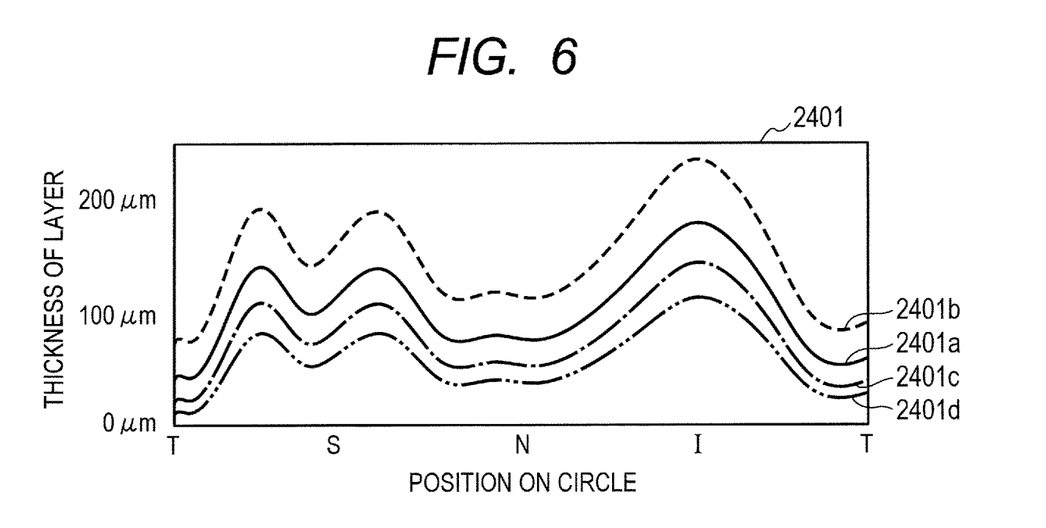
FIG. 6 illustrates a papilla circle map in the second and the third embodiments of the present invention.

Referring now to FIG. 6, the profile of the papilla neural fiber layer to be compared with the normative eye database in the present embodiment will be described. FIG. 6 illustrates a graph 2401 of the neural fiber layer thickness at each position on the circumference of the circle about the papilla. The axis of abscissa indicates the position on the circumference in the map illustrated in FIGS. 4A and 4B, T corresponding to an ear side, S corresponding to an upper side, N corresponding to a nose side, I corresponding to a lower side, and T corresponding to another ear side. The axis of ordinate indicates the thickness of the neural fiber layer. In the graph, a solid line 2401a denotes the thickness of the neural fiber layer obtained from a tomographic image acquired by imaging a subject. Similarly, a dashed line 2401b, a chain line 2401c, and a two-dot chain line 2401d indicate the distributions of the thickness of the neural fiber layer in the normative eye database. The dashed line 2401b denotes the distribution boundary line of 95%, the chain line 2401c denotes the distribution boundary line of 5%, and the two-dot chain line 2401d denotes the distribution boundary line of 1%. The examiner will be able to easily compare the acquired thickness of the neural fiber layer of the subject with the normative eye distribution, thus aiding the examiner with the diagnosis of glaucoma in particular.

The alarm upon replication and the adjustment of the gate position are the same as those of the first embodiment, so that the description thereof will be omitted.

[Third Embodiment]

A fundus examination apparatus according to the present embodiment differs from the first and the second embodiments in an object to be compared. The comparison is performed with the past data of a subject rather than the normative eye database. The schematic configuration of the apparatus and the configurations of a measurement optical system and a spectroscope, and a method for acquiring tomographic images are the same as the first embodiment and the like, so that the descriptions thereof will be omitted.

(Flow of Acquiring a Tomographic Image)

The flow of acquiring images according to the third embodiment is substantially the same as those of the first and the second embodiments, as illustrated in FIG. 3, except for step 1005. Therefore, the description will be given of step 1005.

According to the present embodiment, the previews of a fundus image and a tomographic image are displayed on a display 928 in step 1005. In the first and the second embodiments, the previews show the comparison areas of the normative eye database. In the present embodiment, an image acquisition area of a past examination of a subject is displayed on a preview. This is displayed only if past examination data is available. When the image acquisition area is displayed, the coordinate of the image acquisition area of a past examination is stored together with past examination data relative to the coordinate position of the center of a macula determined by the macula center determining means, or the position of the center of a macula of an image of a past examination is determined and the coordinate of the image acquisition area relative to the center of the macula is obtained for the current image acquisition. On The basis of the information on the coordinate of the image acquisition area of the past examination and the coordinate of the position of the center of the macula on the preview determined by the tomographic image preview, the image acquisition area of the past examination is positioned and displayed on the preview.

This is effective particularly in the case where there is a difference in image acquisition area between the acquisition of a tomographic image in a past examination and the acquisition of a tomographic image in a current examination, because it is desirable to securely include the image acquisition area of the past examination especially when the tomographic image acquisition area of the current examination is wide. Conversely, if the image acquisition area specified in the current examination is narrow, then an alarm or the like is issued to prompt an examiner to change the image acquisition area.

An alarm issued if a comparison area extends beyond a tomographic image acquisition area, and the correction or adjustments thereof are the same as those of the first embodiment, so that The descriptions thereof will be omitted.

Further, the alarm upon a replication and the adjustment of the gate position are the same as those of the first embodiment, so that the description thereof will be omitted.

As described above, the present invention provides a fundus examination apparatus capable of securely acquiring a comparison area by displaying a tomographic image acquisition area at the time of preview in an examination that involves an object to be compared.

In three embodiments described above, the comparison areas have been separately displayed. Alternatively, however, two or three comparison area may be displayed at the same time. If a tomographic image acquisition area is sufficiently large to allow a macula and a papilla to be acquired at the same time, e.g. a tomographic image acquisition area measuring 13 mm in the horizontal direction and 10 mm in the vertical direction, then the macula map area and the papilla neural fiber layer profile area circle may be displayed at the same time. This makes it possible to accomplish comparison in two comparison areas by a single acquisition of a tomographic image, thus reducing inconvenience to a subject timewise.

In the three embodiments described above, the configuration in which the observation of a fundus is carried out by the CCD has been described. Alternatively, however, the observation of a fundus may use a so-called C-scan image created by calculation based on a tomographic image. Further, a so-called SLO may be used, in which a fundus is scanned by a point light source and the intensity of the return light is detected by a high-speed photo detector to obtain a fundus image from the intensity distribution.

[Other Embodiments]

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

Further, the present invention is not limited to the above-described embodiments, and various changes and modifications can be made within the spirit and scope of the present invention. For example, in the above-described embodiments, the descriptions have been given of eyes as the objects to be examined; however, the present invention can be applied to other objects than eyes to be examined, such as skins or organs. In this case, the present invention will have an aspect as a medical device, such as an endoscope, rather than an ophthalmologic apparatus. Preferably, therefore, the present invention is perceived as an examination apparatus exemplified by an ophthalmologic apparatus, and an eye to be inspected is perceived as one example of an object to be examined.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-075143, filed Apr. 1, 2014 which is hereby incorporated by reference herein in its entirety.

What is claimed is:

1. An ophthalmologic apparatus comprising:
one or more processors; and
one or more memories storing instructions which, when executed by the one or more processors, cause the ophthalmologic apparatus to:
continuously acquire a first tomographic image of a fundus of an eye to be inspected;
associate an image acquisition area of a second tomographic image of the fundus, which has been acquired before the first tomographic image is continuously acquired, with an image acquisition area of the continuously acquired first tomographic image so that a position of a characteristic area in the continuously acquired first tomographic image and a position of an area in the second tomographic image are adjusted, the area in the second tomographic image corresponding to the characteristic area in the continuously acquired first tomographic image, the image acquisition area of the second tomographic image being narrower than the image acquisition area of the continuously acquired first tomographic image in a direction orthogonal to a depth direction of the fundus;

control a display unit to preview the continuously acquired first tomographic image as a moving image with the associated image acquisition area of the second tomographic image of the fundus in a superimposing manner; and determine whether or not the associated image acquisition area is included in the image acquisition area of the continuously acquired first tomographic image, wherein in a case that it is determined that the associated image acquisition area is not included in the image acquisition area, the instructions, when executed by the one or more processors, further causes the display unit to display an alarm.

2. The ophthalmologic apparatus according to claim 1, wherein the instructions, when executed by the one or more processors, further cause the ophthalmologic apparatus to:

detect a characteristic area in the continuously acquired first tomographic image; and determine a position at which the associated image acquisition area of the second tomographic image is superimposed in the continuously acquired first tomographic image on the basis of the position of the detected characteristic area that has been detected and a position of a characteristic area in the second tomographic image, which is directed to the position of the detected characteristic area.

3. The ophthalmologic apparatus according to claim 1, wherein the instructions, when executed by the one or more processors, further cause the ophthalmologic apparatus to determine whether or not to display the associated image acquisition area of the second tomographic image on the basis of an acquiring condition input by an examiner.

4. The ophthalmologic apparatus according to claim 1, wherein the instructions, when executed by the one or more processors, further cause the ophthalmologic apparatus to change a position of the image acquisition area of the continuously acquired first tomographic image on the fundus.

5. The ophthalmologic apparatus according to claim 1, wherein the instructions, when executed by the one or more processors, further cause the ophthalmologic apparatus to determine that a mirror image is not included in a tomographic image in the associated area.

6. The ophthalmologic apparatus according to claim 1, wherein the instructions, when executed by the one or more processors, further cause the ophthalmologic apparatus to:

determine whether or not the associated image acquisition area of the second tomographic image is included in the image acquisition area of the continuously acquired first tomographic image; and in a case where it is determined that at least a part of the associated image acquisition area of the second tomographic image is not included in the continuously acquired first tomographic image, cause the display unit to display an alarm.

7. The ophthalmologic apparatus according to claim 1, wherein the display unit is controlled to display two lines representing the associated image acquisition area of the second tomographic image on the continuously acquired first tomographic image in the superimposing manner.

8. An ophthalmologic apparatus, comprising:

one or more processors;

one or more memories storing instructions which, when executed by the one or more processors, cause the ophthalmologic apparatus to:

continuously acquire a first tomographic image of a fundus of an eye to be inspected;

associate an area of a thickness map of a normative eye database, which has been acquired before the first tomographic image is continuously acquired, with an image acquisition area of the continuously acquired first tomographic image so that a position of a characteristic area in the continuously acquired first tomographic image and a position of an area in the thickness map are adjusted, the area in the thickness map corresponding to the characteristic area in the continuously acquired first tomographic image, the associated area of the thickness map of the normative eye database being narrower than an image acquisition area of the continuously acquired first tomographic image in a direction orthogonal to a depth direction of the fundus;

control a display unit to preview the continuously acquired first tomographic image as a moving image with the associated area of the thickness map of the normative eye database in a superimposing manner; and determine whether or not the associated image acquisition area is included in the image acquisition area of the continuously acquired first tomographic image, wherein in a case that it is determined that the associated image acquisition area is not included in the image acquisition area, the instructions, when executed by the one or more processors, further causes the display unit to display an alarm.

9. The ophthalmologic apparatus according to claim 8, wherein the instructions, when executed by the one or more processors, further cause the ophthalmologic apparatus to:

continuously acquire a fundus image of the eye to be inspected;

when the continuously acquired fundus image is previewed on the display unit as a moving image, associate an area corresponding to the thickness map of the normative eye database with the continuously acquired fundus image, to display the area on the moving image in a superimposing manner;

acquire a three-dimensional tomographic image of the eye to be inspected in response to an input for starting an acquisition of the first tomographic image; and control the display unit to display a result of comparing the thickness map of the normative eye database with a thickness map newly obtained from the acquired three-dimensional tomographic image.

10. The ophthalmologic apparatus according to claim 9, wherein the thickness map is selected from a plural kinds of thickness maps corresponding to a plural kinds of diseases.

11. The ophthalmologic apparatus according to claim 9, wherein when the three-dimensional tomographic image including a macula and a papilla of the eye to be inspected is acquired, a map area directed to the macula and a map area directed to the papilla are simultaneously displayed as the area corresponding to the thickness map, on the moving image of the fundus image in superimposing manner.

12. A control method of an ophthalmologic apparatus, the control method comprising:

continuously acquiring a tomographic image of a fundus of an eye to be inspected;

associating an image acquisition area of a second tomographic image of the fundus, which has been acquired before a first tomographic image is continuously acquired, with an image acquisition area of the continuously acquired first tomographic image so that a position of a characteristic area in the continuously acquired first tomographic image and a position of an area in the second tomographic image are adjusted, the area in the second tomographic image corresponding to the characteristic area in the continuously acquired first tomographic image, the image acquisition area of the second tomographic image being narrower than an image acquisition area of the continuously acquired first tomographic image in a direction orthogonal to a depth direction of the fundus;

controlling a display unit to preview the continuously acquired first tomographic image as a moving image with the associated image acquisition area of the second tomographic image of the fundus in a superimposing manner; and determining whether or not the associated image acquisition area is included in the image acquisition area of the continuously acquired first tomographic image, wherein in a case that it is determined that the associated image acquisition area is not included in the image acquisition area, displaying an alarm.

13. A non-transitory storage medium in which a program is stored for causing a computer to execute each step of the control method of an ophthalmologic apparatus according to claim 12.

* * * * *